United States Patent [19]

Bulten et al.

[11] Patent Number: 4,547,320

[45] Date of Patent: Oct. 15, 1985

[54] TIN COMPOUNDS

[75] Inventors: Eric J. Bulten, Blaricum; Hendrik A. Budding, Driebergen, both of Netherlands

[73] Assignee: Nederlandse Centrale Organisatie Voor Toegepast-Natuurwetenschappelijk Onderzoek, Netherlands

[21] Appl. No.: 417,091

[22] Filed: Sep. 13, 1982

Related U.S. Application Data

[63] Continuation of Ser. No. 268,232, May 29, 1981, abandoned.

[30] Foreign Application Priority Data

May 30, 1980 [NL] Netherlands .......................... 8003160
May 8, 1981 [NL] Netherlands .......................... 8102269

[51] Int. Cl.⁴ ................................................. C07F 7/22
[52] U.S. Cl. ..................................... 556/83; 556/104; 556/88; 556/13; 556/28; 556/19; 556/85; 556/86; 556/87; 556/94; 556/26; 556/13
[58] Field of Search ........................................ 260/429.7

[56] References Cited

U.S. PATENT DOCUMENTS 2,867,642 1/1959 Ramsden ...................... 260/429.7
3,226,292 12/1965 Shaver ................................ 424/287

FOREIGN PATENT DOCUMENTS 717973 11/1954 United Kingdom .

OTHER PUBLICATIONS

Sawyer, Organotin Compounds, Marcel Dekker, Inc., N.Y., vol. 1, pp. 198, 204 to 206 & 212 (1971); vol. 3, 949-952 (1971).
Crowe et al., Chemistry & Industry, pp. 200-201 (1980).
Neumann, Die Organische Chemie des Zinns, pp. 183-189 (1967).
Chemical Abstracts 71 20553b (1969).
Janssen et al., Investigations on Organotin Compounds, Part XVIII, pp. 1009-1014 (1963).
Bulten et al., Journal of Organometallic Chemistry, vol. 152, pp. 305-317 (1978).
Gibbons, J. of Organic Chemistry, vol. 26, pp. 2304-2306 (1961).
Luijten, Investigations in the Field of Organotin Chem., p. 116 (1955).
Yutaka Maeda et al., J. Organometallic Chem., v. 10, pp. 247-256 (1967).
Bancroft et al., J. C. S. Dalton, pp. 2355-2358 (1974).
Chemical Abstracts v. 69, 77378m.
J. Organometallic Chem., v. 181 (1), p. 48 (1979).
Chemical Abstracts, v. 84, 90231n.
Chemical Abstracts, v. 71, 31208u (1969).
Chemical Abstracts, v. 75, 37348u (1971).
Table "Unlisted Drugs", vol. 21, No. 3 (1969), p. 41, line q.

*Primary Examiner*—Helen M. S. Sneed
*Attorney, Agent, or Firm*—Brumbaugh, Graves, Donohue & Raymond

[57] ABSTRACT

Tin compounds, a process for the preparation thereof, a process for the preparation of a medicine using such a tin compound for the treatment of malignant tumors in mice as well as the shaped medicine thus obtained.

This invention relates to novel tin compounds, a pharmaceutical composition using the novel compounds and methods for treating cancer using the pharmaceutical composition.

7 Claims, No Drawings

TIN COMPOUNDS

This is a continuation of application Ser. No. 268,232, filed May 29, 1981, now abandoned.

The invention relates to tin compounds, to a process for the preparation thereof, to a process for the preparation of a medicine using such a tin compound for the treatment of malignant tumors in mice, as well as to the shaped medicine thus formed and obtained.

The preparation and application of transition metal complexes is described in Netherlands Patent Application No. 7,904,740, which relates to platinum-diamine complexes. It is stated and elucidated that these platinum-diamine complexes are well suitable for the treatment of cancer, whereas these compounds, in contrast with other well-known platinum compounds, show little or no kidney toxicity.

Very little is known, however, in the field of compounds of main group metals for the present objective.

In Chemistry and Industry, Mar. 1, 1980, pp. 200–201, dialkyltin dihalide complexes are described which have anti-tumor activity. The compounds $(Et_2SnO)_n$, $Cl.Me_2SnOSnMe_2.Cl$ and $Ph_2ClSnOH$ were mentioned, while, in addition to this, research was described of the diethyltin dihalide complex compounds with 2 ligands, namely $Et_2SnX_2.L_2$, where X is a halogen atom and L is phenanthroline or bipyridine. It is stated that these complexes probably do not have a high kidney toxicity.

Now it was found that tin compounds having formula 1 of the formula sheet wherein $R^1$ and $R^2$ represent equal or different, whether or not substituted organic groups, which are bound to tin via a carbon atom, X represents an anionic group, i.e. an inorganic group or an organic group, which, via an electronegative atom (or heteroatom), is bound to tin, $R^3$ is equal to X or equal to $R^1$ or $R^2$, L is a donating ligand, wherein n=0, 1 or 2, are well suitable for the treatment of cancer, while these tin compounds, moreover, display little or no kidney toxicity. The compounds mentioned above in the discussion of the article in Chemistry and Industry are excluded from the above compounds.

Examples of groups $R^1$ and $R^2$ are: a linear or branched alkyl group, a cycloalkyl group, a whether or not substituted aryl group or a whether or not substituted aralkyl group.

Examples of group X are: as inorganic group a hydrogen atom or an acid radical, such as a halogen atom, a sulphate group, a nitrate group, a phosphate group, or a carbonate group, and as organic group an alkoxy group, a thioalkyl group, a hydroxyl group, an ester group, a carboxylate group or an amine group —NRR'—, wherein R and R' are whether or not equal and represent a hydrogen atom, an alkyl group, an aralkyl group or an aryl group.

Examples of the ligand L, which may be whether or not present, are: a nitrogen compound, like $NH_3$, an amine $RNH_2$, $R_2NH$ or $R_3N$, where R=alkyl, aralkyl, aryl, pyridine or an oxygen containing ligand, for instance $Me_2SnCl_2.2O=P(NMe)_3(=Me_2SnCl_2.2HMPT)$, wherein in the above general formula n=1 or 2.

The compounds according to the invention may be prepared by methods known per se, vide "Organometallic Compounds", methods of synthesis, physical constants and chemical reactions (ed. M. Dub), Vol. II "Compounds of germanium, tin and lead", 2nd edition (ed. R. W. Weiss), Springer Verlag, Berlin, 1967.

The invention, furthermore, relates to the preparation of a medicine using a tin compound as described above, as well as to a shaped medicine thus formed and obtained.

Compounds that are preferred according to the invention are those having the formulae 2-11 and 13-18, among which compounds 3, 6-10 and 13-17 are new at the same time.

Extensive research carried out by the National Cancer Institute, Bethesda, USA, and by the European Organization for Research on the Treatment of Cancer, Brussels, Belgium, has shown that the compounds according to the invention display a high therapeutic activity against malignant tumors in mice.

It is possible to replace one Sn-atom by one Ge-atom. An example of such a compound is indicated by formula 12 and has been incorporated in the following Table.

As it appears from this Table, the compounds display interesting anti-tumor activity against, for instance, P 388 lymphocytic leukemia.

TABLE

Anti-tumor activity of tin compounds against P 388 lymphocytic leukemia in mice, according to "Screening data summary interpretation", US National Cancer Institute, Instruction 14 (1978)

| Compound having the formula of the formula sheet | T/C (%)/Dose (mg/kg)[1] |
|---|---|
| 2 | 142/100 |
| $(ClMe_2Sn)_2O$[2] | 141/12.5–123/6.25 |
| 4 | 126/50 |
| $Et_2SnO$[2] | 125/50–154/25–137/12.5–127/6.25 |
| 5 | 155/6.25–126/3.12–134/1.56–133/0.78 |
| 3 | 148/50–135/25–135/12.5–137/6.25 |
| 6 | 147/50–120/25 |
| 7 | 134/100–123/50 |
| $ClPh_2SnOH$[2] | 198/25–163/12.5–135/6.25 |
| 8 | 147/100 |
| 9 | 153/3.12 |
| 10 | 143/3.12 |
| 11 | 130/6.25 |
| 12 | 133/6.25–138/3.12 |
| 13 | 144/12–133/6 |
| 17 | 128/3.2 |
| 18 | 128/16 |

[1]T/C is the ratio survival time (in days) of treated and untreated mice; according to the above-mentioned "Screening data summary interpretation" a compound is considered to be active at T/C values > 120%.
[2]These compounds are known from Chemistry and Industry, 1st March, 1980, pg. 201, as mentioned above.

The invention is further elucidated by means of the following examples.

EXAMPLE I

Diphenylethyltinhydroxide having formula 2 of the formula sheet.

A solution of 16.5 g of iodine in 115 ml of diethyl ether was added dropwise in 30 minutes at 0° C. to a solution of 24.5 g of triphenylethyltin in 100 ml of diethyl ether. After standing for 24 hours at 0° C., the reaction mixture was filtered and concentrated under reduced pressure. Next, under highly reduced pressure (0.6–0.7 mm Hg), the iodobenzene formed was distilled off.

The residue obtained, 28.5 g of diphenylethyltin iodide, was dissolved in 75 ml of diethyl ether and this solution was shaken with a solution of 4 g of potassium hydroxide in 8 ml of water and next with a solution of 2 g of potassium hydroxide in 4 ml of water. The reaction mixture was filtered and evaporated to dryness under reduced pressure (12 mm Hg). The product obtained, 19.5 g, was pulverized with 1 ml of water in a mortar and dried in a desiccator over 50% potassium hydroxide. The yield of pure diphenylethyltin hydroxide amounted to 18.5 g.

Analysis: Calcd. (% by weight): C, 52.71; H, 5.06; Sn, 37.21. Found (% by weight): C, 52.8; H 5.0; Sn, 37.2.

EXAMPLE II

Bis(chloroethylbutyltin)oxide having formula 3 of the formula sheet.

A mixture of 3.8 g of diethyltin oxide, 6 g of dibutyltin dichloride, 30 ml of benzene and 30 ml of petroleum ether (60°–80° C.) was boiled for 5 hours. After filtering, the filtrate was concentrated under reduced pressure. Drying at the air yielded 9.2 g of analytically pure crystalline bis(chloroethylbutyltin)oxide; melting point 38°–42° C.

Analysis: Calcd. (% by weight): C, 29.02; H, 5.68; Sn, 47.79; Cl, 14.28. Found: (% by weight): C, 28.9; H, 5.8; Sn, 47.5; Cl, 14.1.

EXAMPLE III

Dimethyltin dichloride-bis(hexamethylphosphortriamide) having formula 4 of the formula sheet 17.9 g of hexamethylphosphorus triamide (HMPT) were added dropwise to a solution of 4.38 g of dimethyltin dichloride in 100 ml of benzene. A precipitate was produced, while some heat was generated. After having been stirred for 1 hour at ambient temperature, the mixture was heated to boiling temperature and filtered. The clear filtrate was evaporated to 25% of its volume. Filtration and washing with 25 ml of petroleum ether (40°–60° C.) yielded (after drying under reduced pressure) 11.0 g of dimethyltin dichloride bis(hexamethylphosphorus triamide), $Me_2SnCl_2.2HMPT$; melting point 126°–127° C.

Analysis: Calcd. (% by weight): Cl, 12.27; P, 10.72. Found (% by weight): Cl, 12.3; P, 10.8.

EXAMPLE IV

Bis(diethylacetatotin)oxide having formula 5 of the formula sheet

A mixture of 19.2 g of diethyltin oxide, 6 ml of glacial acetic acid and 50 ml of benzene was stirred for 1 hour at ambient temperature. Next, the water formed was distilled off azeotropically with the benzene. The crystalline residue was washed with 10 ml of petroleum ether (40°–60° C.) and dried, whereafter 22.5 g of pure bis(diethylacetatotin)oxide were obtained; melting point (under decomposition) 165° C.

Analysis: Calcd. (% by weight): C, 29.56; H, 5.38; Sn, 48.65. Found (% by weight): C, 29.7; H, 5.5; Sn, 48.2.

EXAMPLE V

Ethylphenyltin oxide having formula 6 of the formula sheet

At −80° C. in 3 hours 12.8 g of bromine were added dropwise to a suspension of 15.2 g of triphenylethyl tin in 40 ml of methanol. The mixture was brought at ambient temperature and under reduced pressure the bromobenzene generated and the solvent were evaporated. The liquid residue was taken up in 50 ml of diethyl ether and stirred with 25 ml of 4N NaOH solution in water. The precipitate formed was filtered off, washed with successively 25 ml of water, 25 ml of acetone and 25 ml of diethyl ether and dried under reduced pressure. Yield 9.0 g of ethylphenyltin oxide; melting point >360° C.

Analysis: Calcd. (% by weight): C, 39.89; H, 4.18; Sn, 49.28. Found (% by weight): C, 40.0; H, 4.0; Sn, 49.1.

EXAMPLE VI

Propylphenyltin oxide having formula 7 of the formula sheet

This compound was prepared according to the procedure described in example V, starting from 11.8 of triphenylpropyltin and 9.6 g of bromine. Yield: 7.2 g of propylphenyltin oxide; melting point >360° C.

Analysis: Calcd. (% by weight): C, 42.41; H, 4.74; Sn, 46.57. Found (% by weight): C, 42.3; H, 4.8; Sn, 46.3.

EXAMPLE VII

Butylphenyltin oxide having formula 8 of the formula sheet

This compound was prepared according to the procedure described in example V, starting from 6.1 g of triphenylbutyl tin and 4.8 g of bromine. Yield 4.1 g butylphenyl tin oxide; melting point >350° C.

Analysis: Calcd. (% by weight): C, 44.67; H, 5.25; Sn, 44.14. Found (% by weight): C, 44.6; H, 5.2; Sn, 44.0.

EXAMPLE VIII

Sec.butylphenyltin oxide having formula 9 of the formula sheet

This compound was prepared according to the procedure described in example V, starting from 12.2 g of triphenylsec.butyltin and 9.6 g of bromine. Yield 7.8. g of sec.butylphenyltin oxide, melting point >350° C.

Analysis: Calcd. (% by weight): C, 44.67; H, 5.25; Sn, 44.14 Found (% by weight): C, 44.5; H, 5.3; Sn, 44.3.

EXAMPLE IX

Propylbenyltin oxide having formula 10 of the formula sheet

This compound was prepared according to the procedure described in example V, starting from 10 g of diphenylpropylbenzyl tin and 7.9 g of bromine. Yield 3.5 g of propylbenzyl tin oxide; melting point >350° C.

Analysis: Calcd. (% by weight): C, 44.67; H, 5.25; Sn, 44.14. Found (% by weight): C, 44.8; H, 5.1; Sn, 44.0.

EXAMPLE X

Bis-(di-p-tolylchlorotin)oxide having formula 13 of the formula sheet

A solution of 5 g of di-p-tolyltin dichloride in 10 ml methanol was added dropwise at room temperature and under quick stirring to 650 ml of distilled water. A white precipitate was formed. After the addition stirring was continued for 15 minutes and then the precipitate was filtered by means of a glass filter, was washed twice with 25 ml of water and washed twice with 25 ml of 40% ethanol. After drying under reduced pressure 3.92 g (85%) of a white product having a melting point of 190°–197° C. were obtained.

Recrystallisation from 50 ml of chloroform yielded 3.01 g (65%) of pure bis-(di-p-tolylchlorotin)oxide having a melting point of 189°–201° C.

Analysis: Calcd. (% by weight): C, 48.83; H, 4.10; Cl, 10.29; O, 2.32; Sn, 34.46. Found (% by weight): C, 49.0; H, 4.2; Cl, 10.0; O, 2.2; Sn, 34.3.

EXAMPLE XI

Bis-(di-o-tolylchlorotin)oxide having formula 14 of the formula sheet

This compound was prepared according to the procedure described in example X, starting from 1.0 g of di-o-tolyltin dichloride dissolved in 3 ml of methanol and added dropwise to 150 ml of distilled water. Yield 0.75 g (81%) pure bis-(di-o-tolylchlorotin)oxide; melting point 142°–148° C.

Analysis: Calcd. (% by weight): C, 48.83; H, 4.10; Cl, 10.29 Found (% by weight): C, 48,6; H, 4.4; Cl, 9.9.

EXAMPLE XII

Bis-(di-p-chlorophenylchlorotin)oxide having formula 15 of the formula sheet

This compound was prepared according to the procedure described in example X, starting from 0.72 g of di-p-chlorophenyltin dichloride dissolved in 3 ml of methanol and dropwise added to 150 ml of distilled water. Yield 0.66 g (81%) of pure bis-(di-p-chlorophenylchlorotin)oxide. The substance exhibits sublimation from 215° C. and melts at about 250° C.

Analysis: Calcd. (% by weight): C, 37.41; H, 2.09; Cl 27.61; Sn, 30.81. Found (% by weight): C, 37.7; H, 2.1; Cl, 27.4; Sn, 30.9.

EXAMPLE XIII

Cyclohexylphenyltin dichloride having formula 16 of the formula sheet

A solution of 9.6 g of bromine in 15 ml of methanol was added dropwise in 4 hours under stirring to a suspension of 13 g of cyclohexyltriphenyltin in 60 ml of methanol at a temperature of −30° C. By means of distillation the reaction mixture was freed of the formed bromobenzene and of the solvent methanol, whereafter 14.7 g of a light yellow liquid remained. This product was taken up in 100 ml of diethyl ether and shaken with 50 ml of 4N NaOH in water. The formed solid substance was sucked by means of a glass filter and washed subsequently with diethyl ether, methanol and water.

Then this solid substance was suspended in 100 ml of diethyl ether and stirred with 50 ml of 4N HCl, wherein a clear, homogeneous two-phase system was formed. The diethyl ether layer was separated, dried over sodium sulphate and evaporated to dryness under reduced pressure. The remaining product, 10 g, was recrystallized from 20 ml of petroleum ether (boiling point 40°–60° C.) and dried, whereafter 8 g (76%) of pure, white crystalline cyclohexylphenyltin dichloride were obtained; melting point 55°–56° C.

Analysis: Calcd. (% by weight): C, 41.20; H, 4.61; Cl, 20.27; Sn, 33.92. Found (% by weight): C, 41.3; H, 4.8; Cl, 20.2; Sn, 34.1.

EXAMPLE XIV

Bis-(cyclohexylphenylchlorotin)oxide having formula 17 of the formula sheet

This compound was prepared according to the procedure described in example X, starting from 3 g of cyclohexylphenyltin dichloride dissolved in 6 ml of methanol and dropwise added to 450 ml of distilled water. Yield 2.3 g (82%); melting point 188°–192° C.

Analysis: Calcd. (% by weight): C, 44.71; H, 5.00; Cl, 11.00; O, 2.48; Sn, 36.81 Found (% by weight): C, 44.9; H, 5.1; Cl, 10.9; O, 2.6; Sn, 36.7.

EXAMPLE XV

Bis-(diphenylnitratotin)oxide having formula 18 of the formula sheet

This compound was prepared according to the prescription of A. N. Fenster and E. I. Becker (J. Organometal Chem., vol. 11 (1968), page 549) and obtained in a yield of 70%.

Analysis: Calcd. (% by weight): C, 42.03; H, 2.94; N, 4.08; O, 16,33. Found (% by weight): C, 42.0; H, 3.0; N, 3.8; O, 15.9.

We claim:

1. A tin compound having the formula:

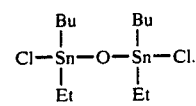

2. A tin compound having the formula:

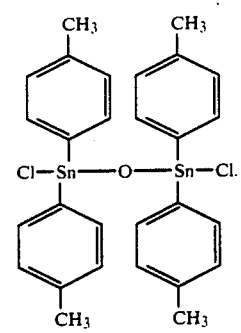

3. A tin compound having the formula:

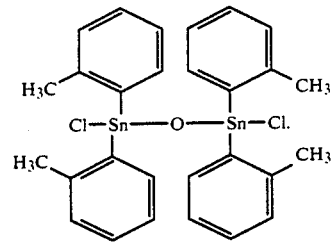

4. A tin compound having the formula:

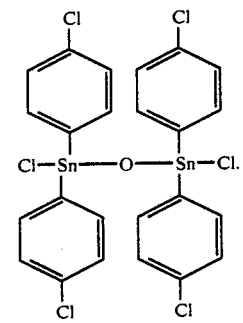

5. A tin compound having the formula:

6. A tin compound having the formula:
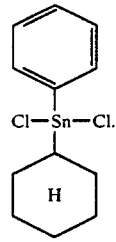
7. A tin compound having the formula:
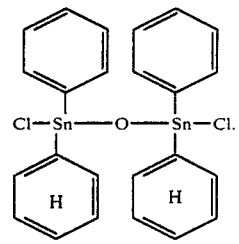
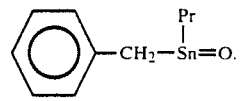
* * * * *

UNITED STATES PATENT AND TRADEMARK OFFICE
CERTIFICATE OF CORRECTION

PATENT NO. : 4,547,320

DATED : October 15, 1985

INVENTOR(S) : Bulten et al.

It is certified that error appears in the above-identified patent and that said Letters Patent is hereby corrected as shown below:

Col. 4, line 40, "Propylbenyltin" should read

--Propylbenzyltin--;

Col. 8, line 10, that portion of the formula reading:

" 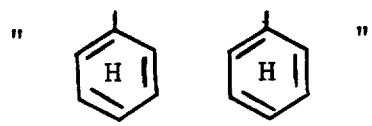 "

should read

-- 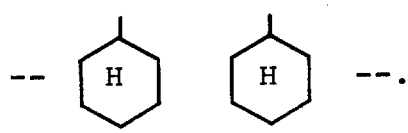 --.

Signed and Sealed this

Fourth Day of March 1986

[SEAL]

Attest:

DONALD J. QUIGG

Attesting Officer

Commissioner of Patents and Trademarks